United States Patent [19]

Moore

[11] 4,400,157
[45] Aug. 23, 1983

[54] DENTAL MIRROR ASSEMBLY

[76] Inventor: Charles E. Moore, 365 N. Church St., Tupelo, Miss. 38801

[21] Appl. No.: 377,668

[22] Filed: May 12, 1982

[51] Int. Cl.³ .............................................. A61C 3/00
[52] U.S. Cl. ........................................................ 433/31
[58] Field of Search ...................................... 433/30, 31

[56] References Cited

U.S. PATENT DOCUMENTS 3,014,279 12/1961 Fosdal .................................... 433/30
3,158,935 12/1964 Rosenthal ............................. 433/30

Primary Examiner—Robert Peshock

[57] ABSTRACT

The dental mirror assembly of the present invention comprises means for securing a conventional mirror head having a mirror surface and means for dispensing a liquid defogging composition in a controlled droplet form onto the mirror surface in response to manual pressure imposed upon the body of the assembly storing the defogging composition.

4 Claims, 4 Drawing Figures

DENTAL MIRROR ASSEMBLY

This invention relates to apparatus for use in combination with a conventional dental mirror for defogging the surface of the mirror.

A dental mirror serves the obvious purpose of providing the dentist or dental technician with a visual image of a localized area within the mouth of a patient under examination. A mirror is required to view and inspect posteria teeth and surrounding gingival tissue. The dental mirror is also used to keep the field of operation under observation during most dental operatory procedures. Notwithstanding its importance as an auxiliary aid, the dental mirror must itself be continually cleaned because the reflected image on the surface of the dental mirror tends to fog up from condensation during normal exhalation. The reflected image may also be distorted or blocked by debris accumulating on the mirror head during a dental procedure. Accordingly, the dental mirror must be repeatedly removed from the operatory site so that it may be wiped clean. Such repeated removal of the mirror continually interrupts the operating procedure and decreases the efficiency of the dentist.

The present invention is directed to a dental assembly which minimizes the susceptibility of the mirror surface to condensation and renders the mirror surface less receptive as a collecting surface for debris. The dental mirror assembly comprises means for securing a conventional mirror head having a mirror surface inclined at a predetermined angle relative to the longitudinal axis of the assembly, a flexible container serving as a reservoir for a liquid defogging composition and a nozzle head having an elongated capillary tube for dispensing a controlled number of droplets of the liquid defogging composition by manually depressing said container.

It is therefor the principle object of the present invention to provide a dental mirror assembly which is capable of controllably dispensing a defogging agent onto the mirror surface to prevent fogging and/or distortion or blockage of the reflected image.

It is a further object of the present invention to provide a dental mirror assembly which is capable of dispensing a defogging agent in a controlled droplet form and in a relatively predetermined measured quantity upon the surface of the mirror to assure a clean and distortion free image over a relatively long time period sufficient to perform a complete dental procedure without interruption.

Other objects and advantages of the present invention will become apparent from the following detailed description of the invention when read in conjunction with the accompanying drawings of which:

Figure 1:
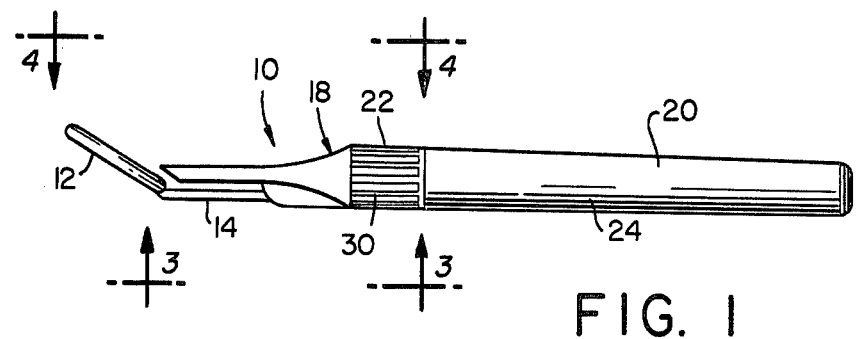
FIG. 1 is an elevation view of the dental mirror assembly of the present invention in combination with a removable dental mirror head.
Figure 3:
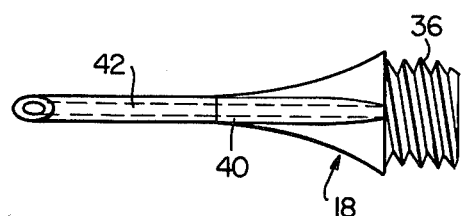
FIG. 3 is an enlarged view of the capillary nozzle dispenser viewed from line 3—3 of FIG. 1 for discharging a liquid defogging composition in droplet form.
Figure 4:
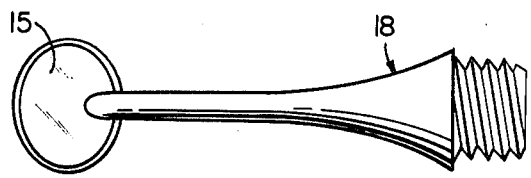
FIG. 4 is an enlarged view of the nozzle dispenser and mirror head viewed from lines 4—4 of FIG. 1.
Figure 2:
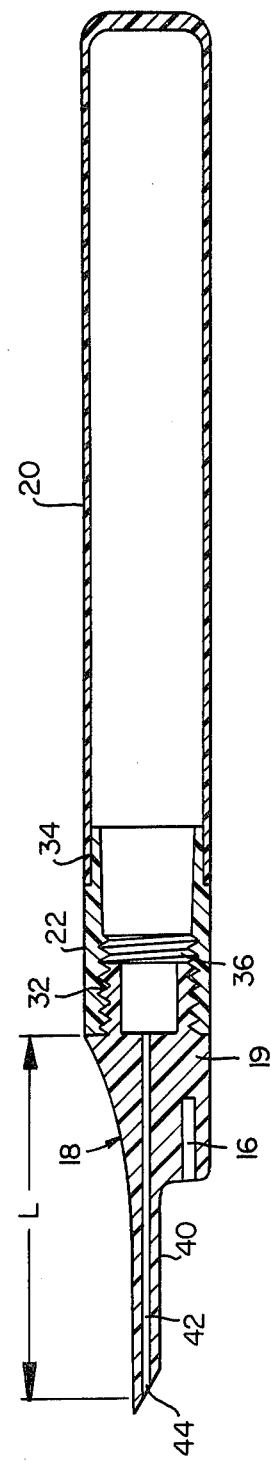
FIG. 2 is a cross sectional view of the dental mirror assembly of FIG. 1.

Referring now in greater detail to the various figures of the drawings wherein like reference characters refer to like parts there is shown in FIG. 1 a dental mirror assembly 10 fully assembled in combination with a conventional mirror head 12. The mirror head 12 includes a depending shank 14 which is removably inserted into a cylindrical opening 16 in the body of the mirror assembly 10 with the axis of the shank in parallel to the longitudinal axis of the assembly 10. The opening 16 is adapted to accommodate a variety of conventional mirror head sizes. The conventional mirror head 12 has a reflecting mirror surface 15 which is inclined at a predetermined angle to the shank 14 and accordingly, at a corresponding angle relative to the longitudinal axis of the mirror assembly 10.

The mirror assembly 10 comprises three major sections including a dispensing nozzle head 18, a container 20 and a coupling member 22 which interconnects the dispensing nozzle head 18 to the container 20. The container 20 is a hollow barrel shaped member which serves as a reservoir for a liquid composition 24 for defogging the mirror surface 15. Although any known defogging liquid composition may be used such as a conventional detergent solution the preferred composition comprises 99.9% by volume water and about 0.1% by volume dimethyl benzyl amonium chloride. The container 20 may be composed of any elastromeric composition which is sufficiently flexible so that it may be manually squeezed to force the liquid composition 24 through the dispensing nozzle head 18 as will be explained in greater detail hereafter. The container should also have sufficient structural integrity to serve as an extension of the shank 14 of the mirror head 12 thereby allowing the mirror assembly 10 to be manipulated in a conventional manner for properly positioning the mirror head and mirror surface to observe the field of operation in the oral cavity.

The coupling member 22 has a splined pheriphery 30 with an internal threaded female section 32 at one end thereof and an extension 34 of slightly reduced diameter relative to the diameter of the container 20 at the other end thereof. The extension 34 should form an interference fit in the container section 20 to form a leak tight connection. Alternatively the container may be bonded or ultrasonically welded to the coupling member at the joint 34. The threaded female section 32 threadably engages the male threaded end 36 of the nozzle head 18. The coupling member 22 thus permits the container 20 to be manually screw threaded for engagement and disengagement to the nozzle head 18. By simply separating the sections, it is possible to fill the container 20 with the defogging composition and reassemble it for use.

The nozzle head 18 is funnel shaped with an elongated snout forming an elongated capillary tube 40 with a bore 42 of a predetermined size diameter such that the combination of the size of the bore 42 and the length L of the tube 40 will result in a discharge of liquid through the nozzle head 18 in droplet form in response to manual pressure on the container 20. The number of discharged droplets of liquid will depend on the pressure applied to the container. The bore 42 should not be more than 1 mm in diameter. The defogging liquid reduces the surface tension of water which minimizes the susceptibility to condensation on the mirror surface and renders it less receptive as a collecting surface for debris. The body 19 of the nozzle head also includes the opening 16 within which the shank 14 of the mirror head 12 is removably held secure. The tube 40 lies parallel to the opening 16 and parallel to the shank 14 with the discharge opening 44 adjacent to the mirror surface 15. The discharge end 46 of the tube 40 is angled to lie in a plane substantially parallel to the surface of the mirror 15.

What is claimed is:

1. A dental mirror assembly comprising: a dispensing nozzle adapted to removably receive a dental mirror-head having a mirror surface, said dispensing nozzle having an elongated funnel shaped snout with a bore of predetermined diameter extending the length of the snout such that the combination of bore diameter and snout length form a capillary like tube for dispensing liquid in controlled droplet form; an elastormeric container for providing a liquid reservoir of a liquid defogging solution and means for removably coupling said container to said dispensing nozzle whereby upon applying pressure to said container liquid from said container is passed into said dispensing nozzle and discharged through said snout in a relatively controlled measure.

2. A dental mirror assembly as defined in claim 1 wherein the distal end of said snout is beveled at an angle lying in a plane parallel to said mirror surface.

3. A dental mirror assembly as defined in claim 2 wherein said coupling means is threadably engaged to said dispensing nozzle.

4. A dental mirror assembly as defined in claim 3 wherein said defogging solution is a composition comprising 99.9% water by volume and about 0.1% dimethgl benzyl amonium chloride by volume.

* * * * *